US010744080B2

(12) United States Patent
Teboul

(10) Patent No.: US 10,744,080 B2
(45) Date of Patent: *Aug. 18, 2020

(54) METHOD FOR THE APPLICATION OF A PIGMENT DYEING COMPOSITION BASED ON SPECIFIC ACRYLIC POLYMER AND ON SILICONE COPOLYMER, AND APPROPRIATE DEVICE

(71) Applicant: L'OREAL, Paris (FR)

(72) Inventor: Karen Teboul, St Mande (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/367,376

(22) PCT Filed: Dec. 20, 2012

(86) PCT No.: PCT/EP2012/076269
§ 371 (c)(1),
(2) Date: Jun. 20, 2014

(87) PCT Pub. No.: WO2013/092788
PCT Pub. Date: Jun. 27, 2013

(65) Prior Publication Data
US 2015/0132243 A1 May 14, 2015

Related U.S. Application Data

(60) Provisional application No. 61/593,041, filed on Jan. 31, 2012.

(30) Foreign Application Priority Data

Dec. 20, 2011 (FR) ...................... 11 62005

(51) Int. Cl.
*A61K 8/895* (2006.01)
*A61K 8/81* (2006.01)
*A61Q 5/06* (2006.01)
*A61Q 1/10* (2006.01)

(52) U.S. Cl.
CPC ............ *A61K 8/895* (2013.01); *A61K 8/8147* (2013.01); *A61K 8/8152* (2013.01); *A61Q 1/10* (2013.01); *A61Q 5/065* (2013.01); *A61K 2800/43* (2013.01); *A61K 2800/594* (2013.01); *A61K 2800/872* (2013.01)

(58) Field of Classification Search
None
See application file for complete search history.

(56) References Cited

U.S. PATENT DOCUMENTS

| | | |
|---|---|---|
| 2,463,611 A | 3/1949 | Green et al. |
| 3,175,993 A | 3/1965 | Weyenberg |
| 3,433,232 A | 3/1969 | Garrett |
| 3,599,647 A | 8/1971 | Fabbri |
| 4,578,266 A | 3/1986 | Tietjen et al. |
| 4,693,935 A | 9/1987 | Mazurek |
| 4,728,571 A | 3/1988 | Clemens et al. |
| 4,772,675 A | 9/1988 | Klosowski et al. |
| 4,871,827 A | 10/1989 | Klosowski et al. |
| 4,888,380 A | 12/1989 | Kamis et al. |
| 4,898,910 A | 2/1990 | Kamis et al. |
| 4,906,719 A | 3/1990 | Chu et al. |
| 4,962,174 A | 10/1990 | Bilgrien et al. |
| 4,972,037 A | 11/1990 | Garbe et al. |
| 5,059,414 A | 10/1991 | Dallal et al. |
| 5,162,410 A | 11/1992 | Sweet |
| 5,246,694 A | 9/1993 | Birthwistle |
| 5,645,609 A | 7/1997 | Andrean et al. |
| 5,799,669 A | 9/1998 | Briggs |
| 5,849,318 A | 12/1998 | Imai et al. |

(Continued)

FOREIGN PATENT DOCUMENTS

| | | |
|---|---|---|
| CA | 711756 A | 6/1965 |
| CN | 101980690 A | 2/2011 |

(Continued)

OTHER PUBLICATIONS

Moss et al., Silicones as a Color-Lock Aid in Rinse-off Hair Care Products, obtained online at: https://pdfs.semanticscholar.org/e78b/faa6983618b3b3896ad83c50e16a675135df.pdf (Year: 2004).*
International Search Report for PCT/EP2012/075421, (published as WO 2013/092381), dated Feb. 26, 2013.
International Search Report for PCT/EP2012/076269, (published as WO 2013/092788), dated Feb. 25, 2013.
International Search Report for PCT/EP2012/075419, (published as WO 2013/092380), dated May 8, 2013.
International Search Report for PCT/EP2012/075423, (published as WO 2013/092382), dated Feb. 28, 2013.
English language abstract for JP 5017710.
English language abstract for JP 7258460.

(Continued)

*Primary Examiner* — Abigail Vanhorn
(74) *Attorney, Agent, or Firm* — The Marbury Law Group, PLLC

(57) ABSTRACT

A subject-matter of the present invention is a method for dyeing human keratinous fibres, which consists in applying a dyeing composition using a container comprising a removable applicator comprising a permeable material through which the composition can pass, the composition being applied by bringing the applicator into contact with the dry or wet fibres, the said composition comprising at least one aqueous dispersion of particles of hybrid hydrophobic film-forming acrylic polymer, at least one linear block silicone copolymer and at least one pigment. The method according to the invention makes it possible to obtain a coloured coating which is persistent towards shampooing operations or washing operations and which leaves the treated fibres individualized, with an improved cosmetic feel; the treated fibres being the hair (roots, sidelocks); non-head hair (beard, moustache); eyelashes or eyebrows.

19 Claims, 1 Drawing Sheet

(56) References Cited

U.S. PATENT DOCUMENTS

| | | | |
|---|---|---|---|
| 5,874,069 A | 2/1999 | Mendolia et al. | |
| 5,919,441 A | 7/1999 | Mendolia et al. | |
| 5,948,393 A | 9/1999 | Tomomasa et al. | |
| 5,961,665 A | 10/1999 | Fishman | |
| 5,981,680 A | 11/1999 | Petroff et al. | |
| 5,990,479 A | 11/1999 | Weiss et al. | |
| 6,013,682 A | 1/2000 | Dalle et al. | |
| 6,024,946 A | 2/2000 | Dubief et al. | |
| 6,051,216 A | 4/2000 | Barr et al. | |
| 6,106,577 A | 8/2000 | Audousset et al. | |
| 6,225,198 B1 | 5/2001 | Alivisatos et al. | |
| 6,606,943 B2 | 8/2003 | De Laforcade | |
| 6,609,457 B1 | 8/2003 | De Laforcade | |
| 7,026,424 B2 | 4/2006 | Schafer et al. | |
| 7,351,405 B2* | 4/2008 | De La Poterie | A61K 8/8152 424/70.11 |
| 7,357,921 B2 | 4/2008 | Giroud | |
| 7,537,120 B1 | 5/2009 | Cardenas | |
| 7,875,265 B2 | 1/2011 | Blin et al. | |
| 7,942,937 B2 | 5/2011 | Brun | |
| 8,124,914 B2 | 2/2012 | Yu | |
| 8,337,822 B2 | 12/2012 | Brun | |
| 2002/0023555 A1 | 2/2002 | Laforcade | |
| 2003/0175229 A1 | 9/2003 | Giroud | |
| 2004/0120906 A1 | 6/2004 | Toumi et al. | |
| 2004/0142831 A1 | 7/2004 | Jager Lezer | |
| 2004/0180021 A1* | 9/2004 | De La Poterie | A61K 8/731 424/70.12 |
| 2004/0182408 A1 | 9/2004 | De LaForcade | |
| 2004/0210024 A1 | 10/2004 | Schafer et al. | |
| 2004/0254325 A1 | 12/2004 | Kuepfer et al. | |
| 2006/0085924 A1 | 4/2006 | Brun | |
| 2006/0093568 A1 | 5/2006 | Blin et al. | |
| 2006/0099164 A1 | 5/2006 | De La Poterie et al. | |
| 2006/0115444 A1 | 6/2006 | Blin et al. | |
| 2006/0116489 A1* | 6/2006 | Lennon | A61K 8/8158 525/479 |
| 2006/0127334 A1 | 6/2006 | Ferrari et al. | |
| 2006/0134032 A1 | 6/2006 | Ilekti et al. | |
| 2006/0134044 A1 | 6/2006 | Blin et al. | |
| 2006/0134051 A1 | 6/2006 | Blin et al. | |
| 2006/0147402 A1 | 7/2006 | Blin et al. | |
| 2006/0147403 A1 | 7/2006 | Ferrari et al. | |
| 2006/0216257 A1 | 9/2006 | Pays et al. | |
| 2007/0044249 A1 | 3/2007 | Lisowski et al. | |
| 2007/0224140 A1 | 9/2007 | Quadir et al. | |
| 2008/0171010 A1 | 7/2008 | Brun | |
| 2009/0151086 A1 | 6/2009 | Brun | |
| 2009/0193595 A1 | 8/2009 | Brun et al. | |
| 2009/0214458 A1 | 8/2009 | Brun et al. | |
| 2011/0005546 A1 | 1/2011 | Muller-Grunow et al. | |
| 2011/0028571 A1 | 2/2011 | Hayakawa | |
| 2011/0097289 A1 | 4/2011 | Viala et al. | |
| 2011/0165104 A1 | 7/2011 | Molenda et al. | |
| 2011/0300092 A1 | 12/2011 | Kambach et al. | |
| 2013/0074864 A1 | 3/2013 | Nuzzo et al. | |
| 2015/0007845 A1* | 1/2015 | Teboul | A45D 19/0008 132/200 |
| 2015/0125413 A1 | 5/2015 | Teboul | |
| 2015/0164196 A1* | 6/2015 | Teboul | A61K 8/26 132/208 |
| 2015/0174041 A1* | 6/2015 | Teboul | A61Q 1/10 424/70.6 |
| 2015/0174051 A1* | 6/2015 | Teboul | A61K 8/26 424/70.6 |

FOREIGN PATENT DOCUMENTS

| | | | |
|---|---|---|---|
| CN | 102274134 A | 12/2011 | |
| EP | 0412704 A2 | 2/1991 | |
| EP | 0412707 A1 | 2/1991 | |
| EP | 0640105 A1 | 3/1995 | |
| EP | 0815836 A2 | 1/1998 | |
| EP | 0874017 A2 | 10/1998 | |
| EP | 1184426 A2 | 3/2002 | |
| EP | 1400234 A1 | 3/2004 | |
| EP | 1649898 A2 | 4/2006 | |
| EP | 2070516 A1 | 6/2009 | |
| EP | 2095810 A1 | 9/2009 | |
| FR | 2679771 A1 | 2/1993 | |
| FR | 2741530 A1 | 5/1997 | |
| FR | 2831430 A1 | 5/2003 | |
| FR | 2833489 A1 | 6/2003 | |
| GB | 2073672 A | 10/1981 | |
| JP | 5017710 A | 1/1993 | |
| JP | 7258460 A | 10/1995 | |
| JP | 9188830 A | 7/1997 | |
| JP | 10-158451 A | 6/1998 | |
| JP | 10158450 A | 6/1998 | |
| JP | 10158541 A | 6/1998 | |
| JP | 2004202251 A | 7/2004 | |
| JP | 2008106067 A | 5/2008 | |
| JP | 2008/247761 A | 10/2008 | |
| JP | 2008247879 A | 10/2008 | |
| JP | 2010524917 A | 7/2010 | |
| JP | 2011026263 A | 2/2011 | |
| WO | 9221316 A1 | 12/1992 | |
| WO | 93/23446 A2 | 11/1993 | |
| WO | 9500578 A1 | 1/1995 | |
| WO | 0196450 A2 | 12/2001 | |
| WO | 03014194 A1 | 2/2003 | |
| WO | 2004028487 A2 | 4/2004 | |
| WO | 2008/142658 A2 | 11/2008 | |
| WO | 2010071777 A1 | 6/2010 | |
| WO | 2013092380 A1 | 6/2013 | |
| WO | 2013092381 A1 | 6/2013 | |
| WO | 2013092382 A1 | 6/2013 | |
| WO | 2014/001390 A1 | 1/2014 | |
| WO | 2014/001391 A1 | 1/2014 | |

OTHER PUBLICATIONS

English language abstract for JP 9188830.
English language abstract for JP 10158541.
English language abstract for JP 10158450.
"Perfumes," Kirk-Othmer Encyclopedia of Chemical Technology, Fourth Edition, vol. 18, 1996, pp. 171-200.
Todd, Charles et al., "Volatile silicone fluids for cosmetic formulations," Cosmetics and Toiletries, Feb. 1990, vol. 105, pp. 53-64.
Dabbousi, B.O., et al., "(CdSe)ZnS Core-Shell Quantum Dots: Synthesis and Characterization of a Size Series of Highly Luminescent Nanocrystallites," Journal of Physical Chemistry B, vol. 101, 1997, pp. 9463-9475.
Peng, Xiaogang et al., "Epitaxial Growth of Highly Luminescent CdSE/CdS Core/Shell Nanocrystals with Photostability and Electronic Accessibility," Journal of the American Chemical Society, vol. 119, No. 30, pp. 7019-7029.
Non-Final Office Action for copending U.S. Appl. No. 14/411,679, dated Oct. 12, 2016.
International Search Report and Written Opinion for PCT/EP2013/063387, dated Jan. 8, 2013.
International Search Report and Written Opinion for PCT/EP2013/063388, dated Jan. 8, 2013.
Non-Final Office Action for copending U.S. Appl. No. 14/367,370, dated Feb. 2, 2016.
Non-Final Office Action for copending U.S. Appl. No. 14/367,382, dated Feb. 24, 2016.
Non-Final Office Action for copending U.S. Appl. No. 14/367,388, dated Jan. 20, 2016.
Final Office Action for co-pending U.S. Appl. No. 14/367,382 (dated Nov. 25, 2016).
Machine translation of Notification of Reasons for Refusal for counterpart Application JP2014-547862, dated Nov. 10, 2016.
Machine translation of Notification of Reasons for Refusal for counterpart Application JP2014-547861, dated Nov. 21, 2016.
Machine translation of Notification of Reasons for Refusal for counterpart Application JP2014-547863, dated Nov. 14, 2016.
Machine translation of First Office Action for counterpart Application CN 201380034562.1, dated Jan. 12, 2016.

(56) References Cited

OTHER PUBLICATIONS

Machine translation of Second Office Action for counterpart Application CN 201380034562.1, dated Nov. 30, 2016.
Machine translation of First Office Action for counterpart Application CN 201380034576.3, dated Dec. 31, 2015.
Machine translation of Second Office Action for counterpart Application CN 201380034576.3, dated Nov. 17, 2016.
Machine translation of Third Office Action for counterpart Application CN 201280062545, dated Apr. 10, 2017.
Office Action for counterpart Application EP 12 799 223.8, dated Jun. 1, 2017.
Non Final Office Action for U.S. Appl. No. 14/367,382, dated Nov. 16, 2017.
Final Office Action for U.S. Appl. No. 14/367,388, dated Sep. 7, 2017.
Final Office Action for U.S. Appl. No. 14/367,370, dated Jun. 16, 2017.
Non Final Office for U.S. Appl. No. 14/411,679, dated Nov. 30, 2017.
Final Office Action for copending U.S. Appl. No. 14/367,370, dated Nov. 3, 2016.
Non-Final Office Action for copending U.S. Appl. No. 14/411,671, dated Jun. 16, 2017.
Final Office Action for copending U.S. Appl. No. 14/367,370, dated Jan. 12, 2018.
Shin-Etsu, "Shin-Etsu Unique Materials," Shin-Etsu, revised Nov. 2010, 20 pages.
Chinese Office Action for counterpart Application No. 201380034576.3, dated Feb. 5, 2018.
Non-Final Office Action for copending U.S. Appl. No. 14/367,388, dated Apr. 9, 2018.
Final Office Action for copending U.S. Appl. No. 14/411,671, dated Apr. 6, 2018.
Final Office Action for copending U.S. Appl. No. 14/411,679, dated Oct. 2, 2018.
Non-Final Office Action for copending U.S. Appl. No. 14/411,671, dated Oct. 3, 2018.
Non-Final Office Action for copending U.S. Appl. No. 14/367,388, dated Oct. 4, 2018.
Final Office Action for copending U.S. Appl. No. 14/367,370, dated Nov. 19, 2018.
Fang, K., et al., "New high molecular weight silicone polyether emulsions for use in personal care applications," IPCOM000200095D, Sep. 27, 2010.
Final Office Action for copending U.S. Appl. No. 14/367,382, dated Aug. 6, 2018.
Final Office Action for co-pending U.S. Appl. No. 14/367,370, dated Jul. 11, 2019.
Final Office Action for co-pending U.S. Appl. No. 14/411,671, dated Apr. 19, 2019.
Final Office Action for co-pending U.S. Appl. No. 14/367,388, dated Apr. 2, 2019.
Non-Final Office Action for co-pending U.S. Appl. No. 14/411,679, dated Apr. 5, 2019.
Notice of Allowance for co-pending U.S. Appl. No. 14/367,388, dated Sep. 5, 2019.
Non-Final Office Action for copending U.S. Appl. No. 14/411,671, dated Mar. 5, 2020.
Non-Final Office Action for co-pending U.S. Appl. No. 14/367,370, dated Jan. 8, 2020.

* cited by examiner

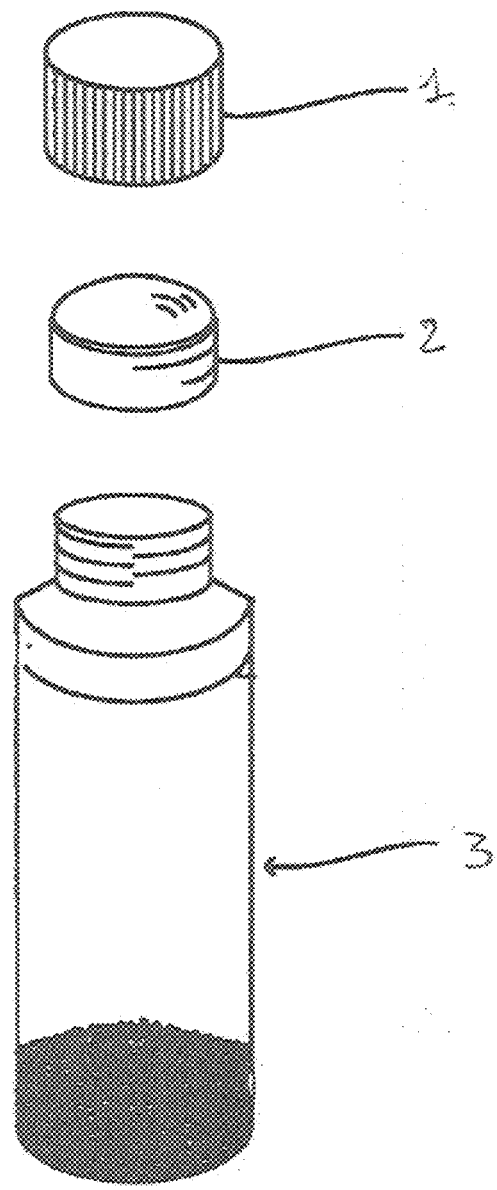

METHOD FOR THE APPLICATION OF A PIGMENT DYEING COMPOSITION BASED ON SPECIFIC ACRYLIC POLYMER AND ON SILICONE COPOLYMER, AND APPROPRIATE DEVICE

This is a national stage application of PCT/EP2012/076269, filed internationally on Dec. 20, 2012, which claims priority to U.S. Provisional Application No. 61/593,041, filed on Jan. 31, 2012, as well as French Application No. 1162005, filed Dec. 20, 2011, all of which are incorporated herein by reference in their entireties.

A subject-matter of the present invention is a method for the application of a composition for dyeing human keratinous fibres, more particularly the hair and very especially roots, sidelocks, beard or moustache hairs, eyelashes and eyebrows. More particularly, the method consists in employing a composition comprising an aqueous dispersion of particles of specific acrylic polymer, a linear block silicone copolymer and a pigment; the composition being stored in a container having a permeable end piece. Another subject-matter of the present invention is an appropriate device for the implementation of the method.

It is known, in the field of the dyeing of keratinous fibres, in particular human keratinous fibres, to dye keratinous fibres by different techniques, in particular starting from dye precursors for permanent colourings or also from direct dyes or pigments for non-permanent colourings.

The present invention is concerned more particularly with the field of non-permanent colouring produced starting from pigments (in other words, starting from colouring substances which are insoluble in the composition in which they are present).

One of the advantages of this type of colouring, in comparison with those deploying direct dyes or dye precursors, is that, in order to be visible, the colouring does not require the use of a stage of prior or simultaneous bleaching of the keratinous fibres, a bleaching stage, carried out with an oxidizing agent, such as hydrogen peroxide or also persalts. This bleaching stage results in not insignificant damage to the keratinous fibres, which detrimentally affects their cosmetic properties. The hair then has a tendency to become rough, more difficult to disentangle and more brittle.

In point of fact, in the case of colouring based on a composition comprising one or more pigments, visible colourings are obtained, also on dark hair since the surface pigment(s) mask the colour of the fibres, whether the colour is natural or artificial.

On the other hand, the disadvantage of methods of this type lies in the temporary nature of the colourings obtained.

The use of pigments to dye keratinous fibres is, for example, described in Patent Application FR 2 741 530, which recommends the use, for the temporary colouring of keratinous fibres, of a composition comprising at least a dispersion of particles of film-forming polymer comprising at least one acid functional group and at least one pigment dispersed in the continuous phase of the said dispersion.

The colourings obtained by this form of colouring exhibit, on the other hand, the disadvantage of having a low resistance to shampooing operations.

Furthermore, it is known to produce coloured coatings of the hair using a composition comprising an electrophilic monomer of cyanoacrylate type and a pigment, in particular in the document EP 1 649 898. Such a composition makes it possible to obtain completely coated and non-greasy hair. However, the coating obtained is not completely satisfactory in the face of external agents, such as washing and perspiration. Furthermore, the coating obtained is sensitive to fatty substances, such as sebum.

It is also possible to colour the hair (coloured coating) using a pressure-sensitive adhesive silicone copolymer, in particular a copolymer based on silicone resin and on silicone fluid. Once deposited on the hair, these copolymers exhibit the advantage of contributing colour in a persistent manner. On the other hand, the hair treated is rather rough to the touch.

Other disadvantages are also met with, encountered during the use of dyeing compositions based on pigments, such as, for example, the need to employ several stages and associated accessories, such as a board, a brush, gloves or drying. In addition, the time taken for the application of the composition may be regarded as too great by the consumer or the hairdresser, in particular if the poorer performance, in particular in terms of persistence, than that of the permanent colourings or non-permanent colourings deploying direct dyes is taken into consideration.

In addition to the fact that these accessories often require a degree of dexterity, indeed even the presence of a third person, in order to use them, they may be inappropriate in some cases, such as that of application to moustache hairs, eyelashes or eyebrows, for example.

Another problem encountered also lies in the accuracy of the application, which is difficult to obtain in some cases, consequently involving losses of composition, if it is necessary to remove the poorly applied product, and also unsightly effects related to the product overflowing onto surfaces which have to remain untreated.

Thus, the aim of the present invention is to provide a device which facilitates the application of a dyeing composition based on pigment(s); this composition in addition giving access to a coloured coating which is persistent towards shampooing operations or washing operations and towards the various attacks which keratinous fibres may be subjected to, without damage to the latter; this coating being in addition homogenous and smooth on the keratinous fibres, leaving the latter completely individualized.

This aim is achieved with the present invention, a subject-matter of which is thus a method for dyeing human keratinous fibres, in particular the hair, preferably roots, sidelocks, non-head hair, in particular beard or moustache hair, eyelashes or eyebrows, which consists in applying a dyeing composition using a container comprising a removable applicator end piece comprising a permeable material through which the composition can pass, the composition being applied by bringing the applicator into contact with the dry or wet fibres, the said composition comprising at least one aqueous dispersion of particles of hybrid hydrophobic film-forming acrylic polymer, at least one linear block silicone copolymer and at least one pigment.

Another subject-matter of the invention is a device appropriate for the implementation of this method.

The term "at least one" is understood to mean "one or more".

The term "comprising a" is understood to mean "comprising at least one", unless otherwise specified.

It is possible, by the use of such a device, to deposit in a simple and localized way the dyeing composition included in it, without the risk of the product running, whether in the context of a self-application or of a dyeing carried out by another person. The application is fast and efficient, without requiring the use of additional accessories, and the impregnation of the fibres is homogenous, whatever their length.

Furthermore, the composition applied makes it possible to obtain a coloured coating which is visible on all types of fibres and which is persistent towards shampooing operations or washing operations while retaining the physical qualities of the keratinous fibre, without it being necessary to carry out a drying other than a natural drying (in contrast to a drying carried out using a heating device). Such a coating is in particular resistant to the external attacks which the fibres may be subjected to, such as blow drying and perspiration. It makes it possible in particular to obtain a smooth and homogeneous deposited layer. Furthermore, it has been found, surprisingly, that the fibres remain completely individualized and can be styled without problems, and that the styling properties contributed to the fibre are persistent towards shampooing operations.

The term "individualized fibres" is understood to mean fibres which, after application of the composition and drying, are not stuck together (or are all separated from one another) and thus do not form clumps, the coating being formed around virtually each fibre.

BRIEF DESCRIPTION OF THE DRAWING

The FIGURE shows an exploded perspective view of a device according to an embodiment.

DYEING COMPOSITION

Aqueous Dispersion of Particles of Hybrid Hydrophobic Film-Forming Acrylic Polymer The term "polymer" Is understood to mean, within the meaning of the invention, a compound corresponding to the repetition of one or more units (these units resulting from compounds known as monomers). This or these unit(s) is (are) repeated at least twice and preferably at least 3 times.

The term "film-forming polymer" is understood to mean a polymer which is capable of forming, by itself alone or in the presence of an additional film-forming agent, a macroscopically continuous film on a support, in particular on keratinous substances, and preferably a cohesive film.

The term "hydrophobic polymer" is understood to mean a polymer having a solubility in water at 25° C. of less than 1% by weight.

The dispersion can be a simple dispersion in the aqueous medium of the composition.

Mention may be made, as specific case of dispersions, of latexes.

The term "hybrid acrylic polymer" is understood to mean, within the meaning of the present invention, a polymer synthesized from at least one compound (i) chosen from monomers having at least one (meth)acrylic acid group and/or esters of these acid monomers and/or amides of these acid monomers and from at least one compound (ii) other than the compounds (i), i.e. which does not comprises (meth)acrylic acid group and/or esters of these acid monomers and/or amides of these acid monomers.

The (meth)acrylic acid esters (also known as (meth)acrylates) are advantageously chosen from alkyl (meth)acrylates, in particular $C_1$-$C_{30}$, preferably $C_1$-$C_{20}$ and better still $C_1$-$C_{10}$ alkyl (meth)acrylates, aryl (meth)acrylates, in particular $C_6$-$C_{10}$ aryl (meth)acrylates, or hydroxyalkyl (meth)acrylates, in particular $C_2$-$C_6$ hydroxyalkyl (meth)acrylates.

Mention may be made, among alkyl (meth)acrylates, of methyl methacrylate, ethyl methacrylate, butyl methacrylate, isobutyl methacrylate, 2-ethylhexyl methacrylate, lauryl methacrylate or cyclohexyl methacrylate.

Mention may be made, among hydroxyalkyl (meth)acrylates, of hydroxyethyl acrylate, 2-hydroxypropyl acrylate, hydroxyethyl methacrylate or 2-hydroxypropyl methacrylate.

Mention may be made, among aryl (meth)acrylates, of benzyl acrylate and phenyl acrylate.

The (meth)acrylic acid esters which are particularly preferred are the alkyl (meth)acrylates.

According to the present invention, the alkyl group of the esters can be either fluorinated or perfluorinated, that is to say that some or all of the hydrogen atoms of the alkyl group are replaced with fluorine atoms.

Mention may be made, as amides of the acid monomers, for example, of (meth)acrylamides and in particular N-alkyl (meth)acrylamides, especially N—($C_2$-$C_{12}$ alkyl)(meth)acrylamides. Mention may be made, among N-alkyl(meth)acrylamides, of N-ethylacrylamide, N-(t-butyl)acrylamide, N-(t-octyl)acrylamide and N-undecylacrylamide.

Mention will be made, as compounds (ii) other than the compounds (i), for example, of the styrene monomers.

In particular, the acrylic polymer can be a styrene/acrylate copolymer and especially a polymer chosen from the copolymers resulting from the polymerization of at least one styrene monomer and at least one $C_1$-$C_{20}$ and preferably $C_1$-$C_{10}$ alkyl acrylate monomer.

Mention may be made, as styrene monomer which can be used in the invention, of styrene or α-methylstyrene and preferably styrene.

The $C_1$-$C_{10}$ alkyl acrylate monomer can be chosen from methyl acrylate, ethyl acrylate, propyl acrylate, butyl acrylate, hexyl acrylate, octyl acrylate or 2-ethylhexyl acrylate.

Mention may be made, as acrylic polymer synthesized with styrene compound, of the styrene/acrylate(s) copolymers sold under the name Joncryl 77 by BASF, under the name Yodosol GH41F by Akzo Nobel and under the name Syntran 5760 CG by Interpolymer.

Mention may also be made, as compound (ii), of the compounds which interact by a process other than the radical polymerization of unsaturated compounds or the compounds resulting from such a process. Such a process can, for example, be a polycondensation. Mention may be made, as polycondensation, of the formation of polyurethanes, polyesters or polyamides. In addition to the acrylic monomer or monomers, the hybrid hydrophobic film-forming polymer of the invention will then comprise the compound resulting from the polycondensation process or the compounds which interact in the polycondensation process.

Mention may in particular be made, as hybrid hydrophobic film-forming acrylic copolymer of this type, of that sold under the reference Hybridur 875 Polymer Dispersion by Air Products and Chemicals.

Use may also be made, as hybrid hydrophobic film-forming acrylic copolymer, of the product sold under the reference Primal HG 1000 by Dow.

The hybrid hydrophobic film-forming acrylic polymer or polymers in aqueous dispersion can be present in a content, as polymeric active materials, ranging from 0.1% to 30% by weight, more particularly from 0.5% to 20% by weight and preferably from 1% to 15% by weight, with respect to the total weight of the composition.

Linear Block Silicone Copolymer

The silicone copolymer used in the composition according to the invention is a linear block copolymer, that is to say an uncrosslinked copolymer, obtained by chain extension and not by crosslinking.

The term "block copolymer" (or "sequential copolymer") denotes a polymer comprising at least two distinct blocks (sequences). Each block of the polymer results from one type of monomer or from several types of different monomers. This means that each block can be composed of a homopolymer or of a copolymer, it being possible for this copolymer constituting the block to be in its turn a random or alternating copolymer.

The silicone copolymer used in the composition according to the invention preferably comprises at least two distinct silicone blocks, each block of the polymer resulting from one type of silicone monomer or from several types of different silicone monomers, such as mentioned below.

It should also be noted that the copolymer is "linear"; in other words, the structure of the polymer is neither branched nor star-shaped nor grafted.

The linear block silicone copolymer is advantageously provided in the form of particles in dispersion in an aqueous medium.

The aqueous dispersion of block copolymer particles is a silicone-in-water (Sil/W) emulsion, the oily globules of which are composed of a silicone of high viscosity, so that these globules appear to form "soft particles".

The size of the linear block silicone copolymer particles can vary widely. Preferably, in the present application, the linear block silicone copolymer particles generally exhibit a number-average size of less than or equal to 2 microns and preferably of less than or equal to 1 micron.

The aqueous dispersions of linear block silicone copolymer particles used in the composition according to the invention can be chosen in particular from those described in the document EP-A-874 017, the teaching of which is incorporated here by reference. According to this document, it is possible in particular to obtain the silicone copolymers constituting these particles by a chain extension reaction in the presence of a catalyst, starting from at least:

(a) one polysiloxane (i) having at least one reactive group and preferably one or two reactive groups per molecule; and (b) one organosilicone compound (ii) which reacts with the polysiloxane (i) by a chain extension reaction.

In particular, the polysiloxane (i) is chosen from the compounds of formula (I):

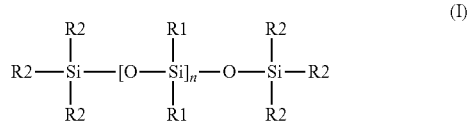

in which $R_1$ and $R_2$ represent, independently of one another, a hydrocarbon group having from 1 to 20 carbon atoms and preferably from 1 to 10 carbon atoms, such as methyl, ethyl, propyl or butyl, or an aryl group, such as phenyl, or a reactive group, and n is an integer greater than 1, provided that there are on average between one and two reactive groups per polymer.

The term "reactive group" is understood to mean any group capable of reacting with the organosilicone compound (ii) to form a block copolymer. Mention may be made, as reactive groups, of hydrogen; aliphatically unsaturated groups and in particular vinyl, allyl or hexenyl groups; the hydroxyl group; alkoxy groups, such as methoxy, ethoxy or propoxy groups; alkoxyalkoxy groups; the acetoxy group; amino groups and their mixtures. Preferably, more than 90% and better still more than 98% of reactive groups are at the chain end, that is to say that the $R_2$ radicals generally constitute more than 90% and even 98% of the reactive groups.

n can in particular be an integer ranging from 5 to 30, preferably from 10 to 30 and better still from 15 to 25.

The polysiloxanes of formula (I) are linear polymers, that is to say comprising few branchings and generally less than 2 mol % of siloxane units. Furthermore, the $R_1$ and $R_2$ groups can optionally be substituted by amino groups, epoxy groups or sulfur-comprising, silicon-comprising or oxygen-comprising groups.

Preferably, at least 80% of the $R_1$ groups are alkyl groups and better still methyl groups.

Preferably, the reactive group $R_2$ at the chain end is an aliphatically unsaturated group and in particular a vinyl group.

Mention may in particular be made, as polysiloxanes (i), of dimethylvinylsiloxy-polydimethylsiloxane, a compound of formula (I) in which the $R_1$ radicals are methyl radicals and the $R_2$ radicals at the chain end are vinyl radicals while the other two $R_2$ radicals are methyl radicals.

The organosilicone compound (ii) can be chosen from polysiloxanes of formula (I) or compounds acting as chain-extending agent. If it is a compound of formula (I), the polysiloxane (i) will comprise a first reactive group and the organosilicone compound (ii) will comprise a second reactive group which will react with the first. If it is a chain-extending agent, it can be a silane, a siloxane (disiloxane or trisiloxane) or a silazane. Preferably, the organosilicone compound (ii) is a liquid organohydropolysiloxane of formula (II):

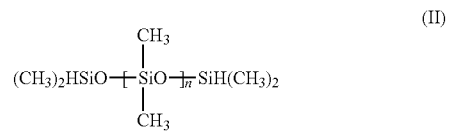

where n is an integer greater than 1 and preferably greater than 10, for example ranging from 2 to 100, preferably from 10 to 30 and better still from 15 to 25. According to a specific embodiment of the invention, n is equal to 20.

The silicone block copolymers used according to the invention are advantageously devoid of oxyalkylene group(s), in particular devoid of oxyethylene and/or oxypropylene group(s).

The catalyst of the reaction between the polysiloxane and the organosilicone compound can be chosen from metals and in particular from platinum, rhodium, tin, titanium, copper and lead. It is preferably platinum or rhodium.

The dispersion of silicone copolymer particles used in the composition according to the invention can in particular be obtained, for example, by mixing (a) water, (b) at least one emulsifier, (c) the polysiloxane (i), (d) the organosilicone compound (ii) and (e) a catalyst. Preferably, one of the constituents (c), (d) or (e) is added last to the mixture, in order for the chain-extending reaction to begin only in the dispersion.

Mention may be made, as emulsifiers capable of being used in the preparation process described above in order to obtain the aqueous dispersion of particles, of non-ionic or ionic (anionic, cationic or amphoteric) emulsifiers. They are preferably non-ionic emulsifiers which can be chosen from polyalkylene glycol ethers of fatty alcohols comprising from 8 to 30 carbon atoms and preferably from 10 to 22 carbon atoms; polyoxyalkylenated and in particular polyoxyethylenated sorbitan alkyl esters, where the alkyl radical comprises from 8 to 30 carbon atoms and preferably from 10 to 22 carbon atoms; polyoxyalkylenated and in particular polyoxyethylenated alkyl esters, where the alkyl radical comprises from 8 to 30 carbon atoms and preferably from 10 to 22 carbon atoms; polyethylene glycols; polypropylene glycols; diethylene glycols; and their mixtures. The amount of emulsifier(s) is generally from 1% to 30% by weight, with respect to the total weight of the reaction mixture.

The emulsifier used to obtain the aqueous dispersion of particles is preferably chosen from polyethylene glycol ethers of fatty alcohols and their mixtures and in particular polyethylene glycol ethers of alcohols comprising 12 or 13 carbon atoms and from 2 to 100 oxyethylene units and preferably from 3 to 50 oxyethylene units, and their mixtures. Mention may be made, for example, of $C_{12}$-$C_{13}$ Pareth-3, $C_{12}$-$C_{13}$ Pareth-23 and their mixtures.

According to a specific embodiment of the invention, the dispersion of silicone copolymer particles is obtained from dimethylvinylsiloxy-polydimethylsiloxane (ou divinyldimethicone), as compound (i), and from the compound of formula (II) with preferably n=20, as compound (ii), preferably in the presence of a catalyst of platinum type, and the dispersion of particles is preferably obtained in the presence of $C_{12}$-$C_{13}$ Pareth-3 and $C_{12}$-$C_{13}$ Pareth-23, as emulsifiers.

Use may in particular be made, as dispersion of silicone copolymer particles, of the product sold under the name HMW 2220 by Dow Corning (CTFA name: divinyldimethicone/dimethicone copolymer/$C_{12}$-$C_{13}$ Pareth-3/$C_{12}$-$C_{13}$ Pareth-23), which is a 60% aqueous dispersion of divinyldimethicone/dimethicone copolymer comprising $C_{12}$-$C_{13}$ Pareth-3 and $C_{12}$-$C_{13}$ Pareth-23, the said dispersion comprising approximately 60% by weight of copolymer, 2.8% by weight of $C_{12}$-$C_{13}$ Pareth-23, 2% by weight of $C_{12}$-$C_{13}$ Pareth-3 and 0.31% by weight of preservatives, the remainder to 100% being water.

The linear block silicone copolymer or copolymers can be present, for example, in an amount, as polymeric active materials, ranging from 0.1% to 30% by weight, better still from 0.5% to 20% by weight and even better still from 1% to 15% by weight, with respect to the total weight of the composition.

According to one embodiment, the hybrid hydrophobic film-forming acrylic polymer or polymers and the linear block silicone copolymer or copolymers are present in a hybrid hydrophobic film-forming acrylic polymer(s) to linear block silicone copolymer(s) ratio by weight (as polymeric active materials) ranging from 0.2 to 10, better still from 0.5 to 5 and even better still from 1 to 3.

When the hybrid hydrophobic film-forming acrylic polymer has a glass transition temperature which is too high for the desired use, a plasticizer can be combined therewith so as to lower this temperature of the mixture used. The plasticizer can be chosen from the plasticizers normally used in the field of application and in particular from compounds which can be solvents for the polymer.

Preferably, the plasticizer has a molecular weight of less than or equal to 5000 g/mol, preferably of less than or equal to 2000 g/mol, preferably of less than or equal to 1000 g/mol and more preferably of less than or equal to 900 g/mol. The plasticizer advantageously has a molecular weight of greater than or equal to 100 g/mol.

Thus, the composition can additionally comprise at least one plasticizing agent. In particular, mention may be made, alone or as a mixture, of the usual plasticizers, such as:
- glycols and their derivatives, such as diethylene glycol ethyl ether, diethylene glycol methyl ether, diethylene glycol butyl ether, diethylene glycol hexyl ether, ethylene glycol ethyl ether, ethylene glycol butyl ether or ethylene glycol hexyl ether;
- polyethylene glycols, polypropylene glycols, polyethylene glycol/polypropylene glycol copolymers and their mixtures, in particular polypropylene glycols of high molecular weight, for example having a molecular weight ranging from 500 to 15 000, such as, for example:
- glycol esters;
- propylene glycol derivatives and in particular propylene glycol phenyl ether, propylene glycol diacetate, dipropylene glycol ethyl ether, tripropylene glycol methyl ether, diethylene glycol methyl ether or dipropylene glycol butyl ether. Such compounds are sold by Dow Chemical under the names Dowanol PPH and Dowanol DPnB;
- acid esters, in particular carboxylic acid esters, such as citrates, phthalates, adipates, carbonates, tartrates, phosphates or sebacates;
- esters resulting from the reaction of a monocarboxylic acid of formula $R_{11}COOH$ with a diol of formula $HOR_{12}OH$ with $R_{11}$ and $R_{12}$, which are identical or different, representing a saturated or unsaturated and linear, branched or cyclic hydrocarbon chain preferably comprising from 3 to 15 carbon atoms and optionally comprising one or more heteroatoms, such as N, O or S, in particular the monoester resulting from the reaction of isobutyric acid and octanediol, such as 2,2,4-trimethyl-1,3-pentanediol, such as that sold under the reference Texanol Ester Alcohol by Eastman Chemical;
- oxyethylenated derivatives, such as oxyethylenated oils, in particular vegetable oils, such as castor oil; and
- their mixtures.

More particularly, the plasticizser can be chosen from esters of at least one carboxylic acid comprising from 1 to 7 carbon atoms and of a polyol comprising at least 4 hydroxyl groups.

The polyol can be a cyclized or non-cyclized monosaccharide-polyhydroxyaldehyde (aldose) or polyhydroxyketone (ketose). The polyol is preferably a cyclized monosaccharide in the hemiacetal form.

The polyol can be a mono- or polysaccharide comprising from 1 to 10 monosaccharide units, preferably from 1 to 4 monosaccharide units and more preferably one or two monosaccharide units. The polyol can be chosen from erythritol, xylitol, sorbitol, glucose, sucrose, lactose or maltose.

The polyol is preferably a disaccharide. Mention may be made, among disaccharides, of sucrose (also known as α-D-glucopyranosyl-(1-2)-β-D-fructofuranose), lactose (also known as β-D-galactopyranosyl-(1-4)-β-D-glucopyranose) and maltose (also known as α-D-glucopyranosyl-(1-4)-β-D-glucopyranose), and preferably of sucrose.

The ester can be composed of a polyol esterified by at least two different monocarboxylic acids or by at least three different monocarboxylic acids.

The ester can be a copolymer of two esters, in particular a copolymer i) of a sucrose substituted by benzoyl groups and ii) of a sucrose substituted by acetyl and/or isobutyryl groups.

The carboxylic acid is preferably a monocarboxylic acid comprising from 1 to 7 carbon atoms and preferably from 1 to 5 carbon atoms, for example chosen from acetic acid, n-propanoic acid, isopropanoic acid, n-butanoic acid, isobutanoic acid, tert-butanoic acid, n-pentanoic acid and benzoic acid.

The ester can be obtained from at least two different monocarboxylic acids. According to one embodiment, the acid is a linear or branched acid which is unsubstituted.

The acid is preferably chosen from acetic acid, isobutyric acid, benzoic acid and their mixtures.

According to a preferred embodiment, the ester is sucrose diacetate hexa(2-methylpropanoate), such as that sold under the name Sustane SAIB Food Grade Kosher by Eastman Chemical.

According to another embodiment, the plasticizer can be chosen from esters of an aliphatic or aromatic polycarboxylic acid and of an aliphatic or aromatic alcohol comprising from 1 to 10 carbon atoms.

The aliphatic or aromatic alcohol comprises from 1 to 10 carbon atoms, preferably from 1 to 8 carbon atoms, for example from 1 to 6 carbon atoms. It can be chosen from R1OH alcohols, such that R1 represents methyl, ethyl, propyl, isopropyl, butyl, hexyl, ethylhexyl, decyl, isodecyl, benzyl or benzyl substituted by an alkyl comprising from 1 to 3 carbon atoms, and their mixtures.

The aliphatic or aromatic polycarboxylic acid preferably comprises from 3 to 12 carbon atoms, preferably from 3 to 10 carbon atoms, preferably from 3 to 8 carbon atoms, for example 6 or 8 carbon atoms.

The aliphatic or aromatic polycarboxylic acid is advantageously chosen from dicarboxylic acids and tricarboxylic acids.

Mention may be made, among aliphatic dicarboxylic acids, of those of formula HOOC—$(CH_2)_n$—COOH, in which n is an integer ranging from 1 to 10, preferably ranging from 2 to 8, for example equal to 2, 4, 6 or 8.

Preference is given to dicarboxylic acids chosen from succinic acid, adipic acid and sebacic acid.

Mention may be made, among aromatic dicarboxylic acids, of phthalic acid.

Mention may be made, among tricarboxylic acids, of triacids which correspond to the formula:

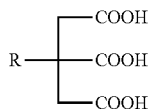

in which R represents an —H, —OH or —OCOR' group in which R' represents an alkyl group having from 1 to 6 carbon atoms. Preferably, R represents an —OCOCH$_3$ group.

The tricarboxylic acid is chosen in particular from acetylcitric acid, butyroylcitric acid or citric acid.

Use may be made, among tricarboxylic acid esters, of esters derived from citric acid (or citrates), such as tributyl acetylcitrate, triethyl acetylcitrate, triethylhexyl acetylcitrate, trihexyl acetylcitrate, trihexyl butyroylcitrate, triisodecyl citrate, triisopropyl citrate, tributyl citrate and tri(2-ethylhexyl) citrate. Mention may be made, as commercial references for plasticizers mentioned above, of the Citroflex range sold by Vertellus, with in particular Citroflex A4 and Citroflex C2.

Mention may be made, among adipic acid esters, of dibutyl adipate and di(2-ethylhexyl) adipate.

Mention may be made, among sebacic acid esters, of dibutyl sebacate, di(2-ethylhexyl) sebacate, diethyl sebacate and diisopropyl sebacate.

Mention may be made, among succinic acid esters, of di(2-ethylhexyl) succinate and diethyl succinate.

Mention may be made, among phthalic acid esters, of benzyl butyl phthalate, dibutyl phthalate, diethylhexyl phthalate, diethyl phthalate and dimethyl phthalate.

Advantageously, the plasticizer or plasticizers can be present in the composition in a content such that the ratio by weight of the hybrid hydrophobic film-forming acrylic polymer or polymers to the plasticizer or plasticizers varies from 0.5 to 100, preferably from 1 to 50 and preferably from 1 to 10.

Pigments

The composition comprises pigments.

Such a composition makes it possible to obtain coloured and persistent coatings, without damaging the keratinous fibres.

The term "pigment" is understood to mean white or coloured particles of any shape which are insoluble in the composition in which they are present.

The pigments which can be used are chosen in particular from organic and/or inorganic pigments known in the art, in particular those which are described in Kirk-Othmer's Encyclopedia of Chemical Technology and in Ullmann's Encyclopedia of Industrial Chemistry.

They can be natural, of natural origin, or not.

These pigments can be provided in the pigment powder or paste form. They can be coated or uncoated.

The pigments can be chosen, for example, from inorganic pigments, organic pigments, lakes, special effect pigments, such as pearlescent agents or glitter, and their mixtures.

The pigment can be an inorganic pigment. The term "inorganic pigment" is understood to mean any pigment which corresponds to the definition of Ullmann's Encyclopedia in the "Inorganic Pigment" chapter. Mention may be made, among inorganic pigments of use in the present invention, of ochres, such as red ochre (clay (in particular kaolinite) and iron hydroxide (for example haematite)), brown ochre (clay (in particular kaolinite) and limonite) or yellow ochre (clay (in particular kaolinite) and goethite); titanium dioxide, optionally surface-treated; zirconium or cerium oxides; zinc, (black, yellow or red) iron or chromium oxides; manganese violet, ultramarine blue, chromium hydrate and ferric blue; or metal powders, such as aluminium powder or copper powder.

Mention may also be made of alkaline earth metal carbonates (such as calcium carbonate or magnesium carbonate), silicon dioxide, quartz and any other compound used as inert filler in cosmetic compositions, provided that these compounds contribute colour or whiteness to the composition under the conditions under which they are employed.

The pigment can be an organic pigment. The term "organic pigment" is understood to mean any pigment which corresponds to the definition of Ullmann's Encyclopedia in the "Organic Pigment" chapter.

The organic pigment can in particular be chosen from nitroso, nitro, azo, xanthene, pyrene, quinoline, anthraquinone, fluoran or phthalocyanine compounds, compounds of metal complex type, or isoindolinone, isoindoline, quinacridone, perinone, perylene, diketopyrrolopyrrole, indigo, thioindigo, dioxazine, triphenylmethane or quinophthalone compounds.

Use may also be made of any inorganic or organic compound which is insoluble in the composition and which is conventional in the cosmetics field, provided that these compounds contribute colour or whiteness to the composition under the conditions under which they are employed, for example guanine, which, according to the refractive index of the composition, is a pigment.

In particular, the white or coloured organic pigments can be chosen from carmine, carbon black, aniline black, azo yellow, quinacridone, phthalocyanine blue, the blue pigments codified in the Color Index under the references CI 42090, 69800, 69825, 73000, 74100 and 74160, the yellow pigments codified in the Color Index under the references CI 11680, 11710, 15985, 19140, 20040, 21100, 21108, 47000 and 47005, the green pigments codified in the Color Index under the references CI 61565, 61570 and 74260, the orange pigments codified in the Color Index under the references CI 11725, 15510, 45370 and 71105, the red pigments codified in the Color Index under the references CI 12085, 12120, 12370, 12420, 12490, 14700, 15525, 15580, 15620, 15630, 15800, 15850, 15865, 15880, 17200, 26100, 45380, 45410, 58000, 73360, 73915 and 75470, or the pigments obtained by oxidative polymerization of indole or phenol derivatives, as are described in Patent FR 2 679 771.

Mention may also be made, as example, of pigment pastes formed of organic pigment, such as the products sold by Hoechst under the names:

Cosmenyl Yellow 10G: Pigment Yellow 3 (CI 11710);
Cosmenyl Yellow G: Pigment Yellow 1 (CI 11680);
Cosmenyl Orange GR: Pigment Orange 43 (CI 71105);
Cosmenyl Red R: Pigment Red 4 (CI 12085);
Cosmenyl Carmine FB: Pigment Red 5 (CI 12490);
Cosmenyl Violet RL: Pigment Violet 23 (CI 51319);
Cosmenyl Blue A2R: Pigment Blue 15.1 (CI 74160);
Cosmenyl Green GG: Pigment Green 7 (CI 74260);
Cosmenyl Black R: Pigment Black 7 (CI 77266).

The pigments in accordance with the invention can also be in the form of composite pigments, as are described in Patent EP 1 184 426. These composite pigments can be composed in particular of particles comprising an inorganic core, at least one binder, which provides for the attachment of the organic pigments to the core, and at least one organic pigment which at least partially covers the core.

The organic pigment can also be a lake. The term "lake" is understood to mean dyes adsorbed onto insoluble particles, the combination thus obtained remaining insoluble during use.

The inorganic substrates onto which the dyes are adsorbed are, for example, alumina, silica, calcium sodium borosilicate, calcium aluminium borosilicate and aluminium.

Mention may be made, among the dyes, of carminic acid. Mention may also be made of the dyes known under the following names: D&C Red 21 (CI 45 380), D&C Orange 5 (CI 45 370), D&C Red 27 (CI 45 410), D&C Orange 10 (CI 45 425), D&C Red 3 (CI 45 430), D&C Red 4 (CI 15 510), D&C Red 33 (CI 17 200), D&C Yellow 5 (CI 19 140), D&C Yellow 6 (CI 15 985), D&C Green (CI 61 570), D&C Yellow 10 (CI 47 005), D&C Green 3 (CI 42 053) or D&C Blue 1 (CI 42 090).

Mention may be made, as examples of lakes, of the product known under the following name: D&C Red 7 (CI 15 850:1).

The pigment can also be a special effect pigment. The term "special effect pigments" is understood to mean pigments which generally create a coloured appearance (characterized by a certain shade, a certain vividness and a certain brightness) which is not uniform and which changes as a function of the conditions of observation (light, temperature, angles of observation, etc.). They thereby contrast with coloured pigments, which provide a conventional opaque, semi-transparent or transparent uniform colour.

There exist several types of special effect pigments: those with a low refractive index, such as fluorescent, photochromic or thermochromic pigments, and those with a higher refractive index, such as pearlescent agents, interferential pigments or glitter.

Mention may be made, as examples of special effect pigments, of pearlescent pigments, such as mica covered with titanium or with bismuth oxychloride, coloured pearlescent pigments, such as mica covered with titanium and with iron oxides, mica covered with iron oxide, mica covered with titanium and in particular with ferric blue or chromium oxide or mica covered with titanium and with an organic pigment as defined above, and pearlescent pigments based on bismuth oxychloride. Mention may be made, as pearlescent pigments, of the following pearlescent agents: Cellini sold by Engelhard (mica-$TiO_2$-lake), Prestige sold by Eckart (mica-$TiO_2$), Prestige Bronze sold by Eckart (mica-$Fe_2O_3$) or Colorona sold by Merck (mica-$TiO_2$—$Fe_2O_3$).

Mention may be also be made of pearlescent agents of gold colour sold in particular by Engelhard under the names of Brilliant Gold 212G (Timica), Gold 222C (Cloisonne), Sparkle Gold (Timica), Gold 4504 (Chromalite) and Monarch Gold 233X (Cloisonne); bronze pearlescent agents sold in particular by Merck under the names Bronze Fine (17384) (Colorona) and Bronze (17353) (Colorona) and by Engelhard under the name Super Bronze (Cloisonne); orange pearlescent agents sold in particular by Engelhard under the names Orange 363C (Cloisonne) and Orange MCR 101 (Cosmica) and by Merck under the names Passion Orange (Colorona) and Matte Orange (17449) (Microna); brown-coloured pearlescent agents sold in particular by Engelhard under the names Nu-Antique Copper 340XB (Cloisonne) and Brown CL4509 (Chromalite); pearlescent agents with a copper glint sold in particular by Engelhard under the name Copper 340A (Timica); pearlescent agents with a red glint sold in particular by Merck under the name Sienna Fine (17386) (Colorona); pearlescent agents with a yellow glint sold in particular by Engelhard under the name Yellow (4502) (Chromalite); red-coloured pearlescent agents with a gold glint sold in particular by Engelhard under the name Sunstone G012 (Gemtone); pink pearlescent agents sold in particular by Engelhard under the name Tan Opale 0005 (Gemtone); black pearlescent agents with a gold glint sold in particular by Engelhard under the name Nu-Antique Bronze 240 AB (Timica); blue pearlescent agents sold in particular by Merck under the name Matte Blue (17433) (Microna); white pearlescent agents with a silvery glint sold in particular by Merck under the name Xirona Silver; golden green pinkish orangey pearlescent agents sold in particular by Merck under the name Indian Summer (Xirona); and their mixtures.

Mention may also be made, still as examples of pearlescent agents, of particles comprising a borosilicate substrate coated with titanium oxide.

Particles comprising a glass substrate coated with titanium oxide are sold in particular under the name Metashine MC1080RY by Toyal.

Finally, mention may also be made, as examples of pearlescent agents, of polyethylene terephthalate glitter, in particular that sold by Meadowbrook Inventions under the name Silver 1P 0.004X0.004 (silvery glitter).

It is also possible to envisage multilayer pigments based on synthetic substrates, such as alumina, silica, calcium sodium borosilicate, calcium aluminium borosilicate and aluminium.

The special effect pigments can also be chosen from reflective particles, that is to say in particular particles having a size, a structure, in particular a thickness of the layer or layers of which it is composed and their physical and chemical nature, and a surface condition which allow them to reflect incident light. This reflection may, if appropriate, have an intensity sufficient to create, at the surface of the composition or mixture, when the latter is applied to the substrate to be made up, highlight points visible to the naked eye, that is to say more luminous points which contrast with their surroundings by appearing to sparkle.

The reflective particles can be selected so as not to detrimentally affect, to a significant extent, the colouring effect generated by the colouring agents which are combined with them and more particularly so as to optimize this effect in terms of colour rendition. They can more particularly have a yellow, pink, red, bronze, orangey, brown, gold and/or coppery colour or glint.

These particles can exhibit varied forms and can in particular be in the platelet or globular form, especially the spherical form.

The reflective particles, whatever their form, may or may not exhibit a multilayer structure and, in the case of a multilayer structure, may exhibit, for example, at least one layer of uniform thickness, in particular of a reflective material.

When the reflective particles do not exhibit a multilayer structure, they can be composed, for example, of metal oxides, in particular of titanium or iron oxides obtained synthetically.

When the reflective particles exhibit a multilayer structure, they can, for example, comprise a natural or synthetic substrate, in particular a synthetic substrate, at least partially coated with at least one layer of a reflective material, in particular of at least one metal or metal material. The substrate can be made of one or more organic and/or inorganic materials.

More particularly, it can be chosen from glasses, ceramics, graphite, metal oxides, aluminas, silicas, silicates, in particular aluminosilicates and borosilicates, synthetic mica and their mixtures, this list not being limiting.

The reflective material can comprise a layer of metal or of a metal material.

Reflective particles are described in particular in the documents JP-A-09188830, JP-A-10158450, JP-A-10158541, JP-A-07258460 and JP-A-05017710.

Mention may also be made, still by way of example of reflective particles comprising an inorganic substrate coated with a layer of metal, of the particles comprising a borosilicate substrate coated with silver.

Particles comprising a glass substrate coated with silver, in the form of platelets, are sold under the name Microglass Metashine REFSX 2025 PS by Toyal. Particles comprising a glass substrate coated with nickel/chromium/molybdenum alloy are sold under the names Crystal Star GF 550 and GF 2525 by this same company.

Use may also be made of particles comprising a metal substrate, such as silver, aluminium, iron, chromium, nickel, molybdenum, gold, copper, zinc, tin, magnesium, steel, bronze or titanium, the said substrate being coated with at least one layer of at least one metal oxide, such as titanium oxide, aluminium oxide, iron oxide, cerium oxide, chromium oxide, silicon oxides and their mixtures.

Mention may be made, as examples, of aluminium powder, bronze powder or copper powder coated with $SiO_2$ sold under the name Visionaire by Eckart.

Mention may also be made of pigments with an interference effect which are not attached to a substrate, such as liquid crystals (Helicones HC from Wacker) or interference holographic glitter (Geometric Pigments or Spectra f/x from Spectratek). Special effect pigments also comprise fluorescent pigments, whether these are substances which are fluorescent in daylight or which produce ultraviolet fluorescence, phosphorescent pigments, photochromic pigments, thermochromic pigments and quantum dots, for example sold by Quantum Dots Corporation.

Quantum dots are luminescent semiconductor nanoparticles capable of emitting, under light excitation, radiation exhibiting a wavelength of between 400 nm and 700 nm. These nanoparticles are known from the literature. In particular, they can be synthesized according to the processes described, for example, in U.S. Pat. No. 6,225,198 or 5,990,479, in the publications which are cited therein and in the following publications: Dabboussi B. O. et al., "(CdSe) ZnS core-shell quantum dots: synthesis and characterisation of a size series of highly luminescent nanocristallites", Journal of Physical Chemistry B, vol. 101, 1997, pp 9463-9475, and Peng, Xiaogang et al., "Epitaxial growth of highly luminescent CdSe/CdS core/shell nanocrystals with photostability and electronic accessibility", Journal of the American Chemical Society, vol. 119, No. 30, pp 7019-7029.

The variety of the pigments which can be used in the present invention makes it possible to obtain a rich palette of colours and also specific optical effects, such as metallic effects or interference effects.

The size of the pigment used in the cosmetic composition according to the present invention is generally between 10 nm and 200 µm, preferably between 20 nm and 80 µm and more preferably between 30 nm and 50 µm.

The pigments can be dispersed in the product by virtue of a dispersing agent.

The dispersing agent serves to protect the dispersed particles from the agglomeration or flocculation thereof. This dispersing agent can be a surfactant, an oligomer, a polymer or a mixture of several of them carrying one or more functionalities having a strong affinity for the surface of the particles to be dispersed. In particular, they can become attached physically or chemically to the surface of the pigments. These dispersants additionally exhibit at least one functional group compatible with or soluble in the continuous medium. Use is made in particular of esters of 12-hydroxystearic acid, in particular, and of $C_8$ to $C_{20}$ fatty acid and of polyol, for instance glycerol or diglycerol, such as poly(12-hydroxystearic acid) stearate with a molecular weight of approximately 750 g/mol, such as that sold under the name of Solsperse 21 000 by Avecia, polyglyceryl-2 dipolyhydroxystearate (CTFA name), sold under the reference Dehymyls PGPH by Henkel, or polyhydroxystearic acid, such as that sold under the reference Arlacel P100 by Uniqema, and their mixtures.

Mention may be made, as other dispersant which can be used in the compositions of the invention, of the quaternary ammonium derivatives of polycondensed fatty acids, such as Solsperse 17 000, sold by Avecia, or polydimethylsiloxane/ oxypropylene mixtures, such as those sold by Dow Corning under the references DC2-5185 and DC2-5225 C.

The pigments used in the cosmetic composition according to the invention can be surface-treated with an organic agent.

Thus, the pigments surface-treated beforehand of use in the context of the invention are pigments which have been completely or partially subjected to a surface treatment of chemical, electronic, electrochemical, mechanochemical or mechanical nature with an organic agent, such as those which are described in particular in Cosmetics and Toiletries, February 1990, Vol. 105, pp 53-64, before being dispersed in the composition in accordance with the invention. These organic agents can, for example, be chosen from waxes, for example carnauba wax and beeswax; fatty acids, fatty alcohols and their derivatives, such as stearic acid, hydroxystearic acid, stearyl alcohol, hydroxystearyl alcohol, lauric acid and their derivatives; anionic surfactants; lecithins; sodium, potassium, magnesium, iron, titanium, zinc or aluminium salts of fatty acids, for example aluminium stearate or laurate; metal alkoxides; polyethylene; (meth) acrylic polymers, for example polymethyl methacrylates; polymers and copolymers comprising acrylate units; alkanolamines; silicone compounds, for example silicones or polydimethylsiloxanes; fluorinated organic compounds, for example perfluoroalkyl ethers; or fluorosilicone compounds.

The surface-treated pigments of use in the cosmetic composition according to the invention may also have been treated with a mixture of these compounds and/or have undergone several surface treatments.

The surface-treated pigments of use in the context of the present invention can be prepared according to surface treatment techniques well known to a person skilled in the art or found as such commercially.

Preferably, the surface-treated pigments are covered with an organic layer.

The organic agent with which the pigments are treated can be deposited on the pigments by solvent evaporation, chemical reaction between the molecules of the surface agent or creation of a covalent bond between the surface agent and the pigments.

The surface treatment can thus be carried out, for example, by chemical reaction of a surface agent with the surface of the pigments and creation of a covalent bond between the surface agent and the pigments or fillers. This method is described in particular in U.S. Pat. No. 4,578,266.

Preferably, use will be made of an organic agent covalently bonded to the pigments.

The agent for the surface treatment can represent from 0.1% to 50% by weight, preferably from 0.5% to 30% by weight and more preferentially still from 1% to 10% by weight of the total weight of the surface-treated pigments.

Preferably, the surface treatments of the pigments are chosen from the following treatments:

a PEG-silicone treatment, such as the AQ surface treatment sold by LCW;

a methicone treatment, such as the SI surface treatment sold by LCW;

a dimethicone treatment, such as the Covasil 3.05 surface treatment sold by LCW;

a dimethicone/trimethylsiloxysilicate treatment, such as the Covasil 4.05 surface treatment sold by LCW;

a magnesium myristate treatment, such as the MM surface treatment sold by LCW;

an aluminium dimyristate treatment, such as the MI surface treatment sold by Miyoshi;

a perfluoropolymethylisopropyl ether treatment, such as the FHC surface treatment sold by LCW;

an isostearyl sebacate treatment, such as the HS surface treatment sold by Miyoshi;

a perfluoroalkyl phosphate treatment, such as the PF surface treatment sold by Daito;

an acrylate/dimethicone copolymer and perfluoroalkyl phosphate treatment, such as the FSA surface treatment sold by Daito;

a polymethylhydrosiloxane/perfluoroalkyl phosphate treatment, such as the FS01 surface treatment sold by Daito;

an acrylate/dimethicone copolymer treatment, such as the ASC surface treatment sold by Daito;

an isopropyl titanium triisostearate treatment, such as the ITT surface treatment sold by Daito;

an acrylate copolymer treatment, such as the APD surface treatment sold by Daito;

a perfluoroalkyl phosphate/isopropyl titanium triisostearate treatment, such as the PF+ITT surface treatment sold by Daito.

Preferably, the pigment is chosen from inorganic pigments or inorganic/organic mixed pigments.

The amount of pigment(s) can vary from 0.01% to 30% by weight, more particularly from 0.05% to 20% by weight and preferably from 0.1% to 15% by weight, with respect to the total weight of the composition.

The composition of the invention can comprise other coloured or colouring entities, such as direct dyes or dye precursors.

Thickening Agent

According to a preferred embodiment, the composition according to the invention comprises at least one thickening agent chosen from polymeric or non-polymeric and inorganic or organic thickening agents, and their mixtures.

The term "thickener" is understood to mean a compound which modifies the rheology of the medium in which it is incorporated.

According to a specific embodiment of the invention, the composition comprises at least one inorganic thickener.

Preferably, the thickener or thickeners is/are chosen from fumed silica, clays or their mixtures.

The fumed silicas can be obtained by high-temperature pyrolysis of a volatile silicon compound in an oxhydric flame, producing a finely divided silica. This process makes it possible in particular to obtain hydrophilic silicas which exhibit a large number of silanol groups at their surface. Such hydrophilic silicas are sold, for example, under the names Aerosil 130®, Aerosil 200®, Aerosil 255®, Aerosil 300® and Aerosil 380® by Degussa and Cab-O-Sil HS-5®, Cab-O-Sil EH-5®, Cab-O-Sil LM-130®, Cab-O-Sil MS-55® and Cab-O-Sil M-5® by Cabot.

It is possible to chemically modify the surface of the said silica via a chemical reaction which brings about a reduction in the number of silanol groups. It is possible in particular to replace silanol groups with hydrophobic groups: a hydrophobic silica is then obtained.

The hydrophobic groups can be:

trimethylsiloxyl groups, which are obtained in particular by treating fumed silica in the presence of hexamethyldisilazane. Silicas thus treated are known as "Silica silylate" according to the CTFA ($6^{th}$ edition, 1995). They are sold, for example, under the references Aerosil R812® by Degussa and Cab-O-Sil TS-530® by Cabot.

dimethylsilyloxyl or polydimethylsiloxane groups, which are obtained in particular by treating fumed silica in the presence of polydimethylsiloxane or dimethyldichlorosilane. Silicas thus treated are known as "Silica dimethyl silylate" according to the CTFA ($6^{th}$ edition, 1995). They are sold, for example, under the references Aerosil R972® and Aerosil R974® by Degussa and Cab-O-Sil TS-610® and Cab-O-Sil TS-720® by Cabot.

The fumed silica preferably exhibits a particle size which can be nanometric to micrometric, for example ranging from approximately 5 to 200 nm.

Clays are well known products which are described, for example, in the publication "Minéralogie des argiles" [Mineralogy of Clays], S. Caillère, S. Hénin and M. Rautureau, 2nd Edition, 1982, Masson.

Clays are silicates including a cation which can be chosen from calcium, magnesium, aluminium, sodium, potassium or lithium cations, and their mixtures.

Mention may be made, as examples of such products, of clays of the family of the smectites, such as montmorillonites, hectorites, bentonites, beidellites or saponites, and also of the family of the vermiculites, stevensite or chlorites.

These clays can be of natural or synthetic origin. Use is preferably made of clays which are cosmetically compatible with and acceptable to keratinous substances.

Mention may be made, as clay which can be used according to the invention, of synthetic hectorites (also known as laponites), such as the products sold by Laporte under the name Laponite XLG, Laponite RD and Laponite RDS (these products are sodium magnesium silicates and in particular lithium magnesium sodium silicates); bentonites, such as the product sold under the name Bentone HC by Rheox; magnesium aluminium silicates, in particular hydrated, such as the product sold by R.T. Vanderbilt Company under the name Veegum Ultra, or calcium silicates and in particular that in synthetic form sold by the company CELITE ET WALSH ASS under the name Micro-Cel C.

The organophilic clay can be chosen from montmorillonite, bentonite, hectorite, attapulgite or sepiolite, and their mixtures. The clay is preferably a bentonite or a hectorite.

These clays can be modified with a chemical compound chosen from quaternary ammoniums, tertiary amines, amine acetates, imidazolines, amine soaps, fatty sulfates, alkylarylsulfonates, amine oxides and their mixtures.

Mention may be made, as organophilic clays, of quaternium-18 bentonites, such as those sold under the names Bentone 3, Bentone 38 and Bentone 38V by Rheox, Tixogel VP by United Catalyst and Claytone 34, Claytone 40 and Claytone XL by Southern Clay; stearalkonium bentonites, such as those sold under the names Bentone 27 by Rheox, Tixogel LG by United Catalyst and Claytone AF and Claytone APA by Southern Clay; and quaternium-18/benzalkonium bentonites, such as those sold under the names Claytone HT and Claytone PS by Southern Clay.

The thickener can also be chosen from organic compounds.

Mention may be made, for example, of the following polymeric or non-polymeric products:

$C_{10}$-$C_{30}$ fatty amides, such as lauric acid diethanolamide, the polyglyceryl (meth)acrylate polymers sold under the Hispagel or Lubragel names by Hispano Quimica or Guardian, polyvinylpyrrolidone, polyvinyl alcohol, crosslinked acrylamide polymers and copolymers, such as those sold under the names PAS 5161 or Bozepol C by Hoechst or Sepigel 305 by SEPPIC, or alternatively the crosslinked methacryloyloxyethyltrimethylammonium chloride homopolymers sold under the name Salcare SC95 by Allied Colloid, associative polymers and in particular associative polyurethanes.

Such thickeners are described in particular in Application EP-A-1 400 234.

Preferably, the composition comprises at least one inorganic thickening agent which is preferably chosen from clays and more advantageously still from smectites.

The thickening agent is present in the composition in a total content ranging from 0.1% to 10% by weight, with respect to the weight of the composition.

The composition according to the invention comprises water, which can preferably be present in a content ranging from 20% to 98% by weight, with respect to the weight of the composition.

The compositions can also comprise at least one agent commonly used in cosmetics, for example chosen from reducing agents, fatty substances, organic solvents or oils, softening agents, anti-foaming agents, moisturizing agents, UV screening agents, peptizing agents, solubilizing agents, fragrances, anionic, cationic, non-ionic or amphoteric surfactants, proteins, vitamins, propellants, oxyethylenated or non-oxyethylenated waxes, paraffins or $C_{10}$-$C_{30}$ fatty acids, such as stearic acid or lauric acid.

The above additives are generally present in an amount for each of them of between 0.01% and 20% by weight, with respect to the weight of the composition.

Of course, a person skilled in the art will take care to choose this or these optional additive(s) so that the advantageous properties intrinsically attached to the formation of the coating in accordance with the invention are not, or not substantially, detrimentally affected.

The composition according to the invention can be provided in particular in the form of a suspension, a dispersion, a gel, an emulsion, in particular an oil-in-water (O/W), water-in-oil (W/O) or multiple (W/O/W or polyol/O/W or O/W/O) emulsion, a cream, a foam, a stick, a dispersion of vesicles, in particular of ionic or non-ionic lipids, a two-phase or multiphase lotion, a spray or a paste. The composition can also be provided in the form of a lacquer.

A person skilled in the art can choose the appropriate formulation form, and also its method of preparation, on the basis of his general knowledge, taking into account first the nature of the constituents used, in particular their solubility in the support, and secondly the application envisaged for the composition.

Device

As indicated above, the composition is present in a container comprising a removable applicator end piece comprising a permeable material through which the said composition can pass.

Advantageously, the container further comprises a removable stopper fitted to the said applicator on the container.

Reference may be made to the FIGURE, which, however, is presented only be way of indication and without any implied limitation of the device. The FIGURE shows an exploded perspective view of a container 3 comprising a removable applicator end piece 2 comprising a permeable material through which the said composition can pass and a removable stopper 1 that fits to the said applicator on the container.

Such a device employed in the process according to the invention is described in particular in U.S. Pat. No. 5,961,665 (Fishmann).

Advantageously, the container comprising the composition can comprise an annular narrowing to help it to be grasped in the hand.

The container can, for example, be in the form of a small flexible or rigid bottle. Alternatively, a bottle made of thermoplastic material, for example of PET, can be used. The bottle has, for example, a capacity of 6 ml. The bottle comprises a side wall in the form of a cylinder of revolution, one end of which is closed by a base. The second end is formed by a portion having a narrowed diameter, which ends in a free edge defining an opening.

An applicator end piece is provided to be fitted onto the bottle and to be snap-fastened or screwed onto the above-mentioned opening of the bottle.

The end piece is provided in the form of a substantially cylindrical shell having a uniform circular diameter over a large part of its length. It could have any other form, for example a frustoconical form, becoming progressively smaller until it defines a circular portion.

The end piece has, for example, a diameter of approximately 15 mm. Axial ribs can be provided on the internal wall of the shell. They can comprise a radial indentation which, in the fitted position of the shell, will become housed in the opening of the bottle, thereby allowing the shell to be snap-fastened onto the bottle. Alternatively, it is possible to provide for the internal wall of the shell to be supplied with a thread intended to interact with a thread provided on the neck of the bottle.

The applicator end piece can comprise a cylindrical skirt, which provides sealing between the opening of the bottle and the outlet orifice.

The applicator end piece is advantageously obtained by moulding a single piece of a preferably thermoplastic material, in particular of a polyethylene, of a polypropylene, of a polyethylene terephthalate, of a polyvinyl chloride or of a polyamide.

The applicator, in particular in the form of a pad, makes it possible to regulate the flow of composition which it allows to pass, and to prevent it from running.

Advantageously, the applicator, in particular pad, comprises a valve stem and an integral spring which makes possible the dispensing of an appropriate amount of composition.

The permeable material through which the dyeing composition can pass can be a felt, a flock coating, a foam or an end piece of roll-on type (the roll-on can be a sphere or a cylinder or else can have an ovoid shape of the rugby ball type) and preferably a foam, preferably a polymeric foam, for example made of polyurethane.

For use, the stopper is removed in order to allow the product to be applied by the applicator.

The user takes hold of the bottle, inverts it or tips it and applies the end piece to the fibres to be coloured. It then suffices for the user to apply pressure, one or more times, to the applicator end piece (padding).

Application Method

The composition described above, included in a container also as described above, can be employed on dry or wet keratinous fibres and also on any type of fibre, light or dark, natural or dyed, or permanent-waved, bleached or straightened.

According to a specific embodiment of the method of the invention, the fibres are washed before application of the composition described above.

The application to the fibres can be carried out by any conventional means, in particular using a comb, a brush, including a fine brush, or the fingers.

After the application of the composition, the fibres can be left to dry or dried, for example at a temperature of greater than or equal to 30° C. According to a specific embodiment, this temperature is greater than 40° C. According to a specific embodiment, this temperature is greater than 45° C. and less than 220° C.

The drying, if it is employed, can be carried out immediately after the application or after a leave-in time which can range from 1 minute to 30 minutes.

Preferably, if the fibres are dried, they are dried, in addition to a contribution of heat, with a flow of air. This flow of air during the drying makes it possible to improve the individualization of the coating.

During the drying, a mechanical action can be exerted on the locks, such as combing, brushing or running the fingers through the hair. This operation can likewise be carried out once the fibres have dried, naturally or otherwise.

The drying stage of the method of the invention can be carried out with a hood dryer, a hair dryer, a straightening iron, a Climazone, etc.

When the drying stage is carried out with a hood dryer or a hair dryer, the drying temperature is between 40° C. and 110° C. and preferably between 50° C. and 90° C.

When the drying stage is carried out with a smoothing iron, the drying temperature is between 110° C. and 220° C. and preferably between 140° C. and 200° C.

Once the drying is complete, a final rinsing or shampooing operation can optionally be carried out.

The invention will be illustrated more fully with the aid of the non-limiting examples that follow. Unless otherwise mentioned, the amounts indicated are expressed in grams.

EXAMPLES

Composition Examples

| Composition A | |
|---|---|
| Styrene/acrylates copolymer in aqueous dispersion, sold by BASF under the name Joncryl 77. | 21.2 g i.e. 10% as AM |
| Divinyldimethicone/dimethicone copolymer in aqueous emulsion, sold by Dow Corning under the reference HMW 2220 Non-Ionic Emulsion | 8.3 g i.e. 5% as AM |
| Black 2 in aqueous dispersion, from Daito Kasei Kogyo under the name WD-CB2 | 9 g, i.e. 2.25% as AM |
| Water | q.s. 100 g |

0.6 g of composition A is applied, with the applicator according to the invention, to a moustache.

After a few seconds, the fibres are dry and coloured and the black colour is homogenous and persistent towards several shampooing operations.

A dyed moustache is obtained, the hairs of which are individualized and the colour of which is persistent towards washing.

| Composition B | |
|---|---|
| Styrene/acrylates copolymer in aqueous dispersion, sold by BASF under the name Joncryl 77. | 20 g, i.e. 9.43% as AM |
| Divinyldimethicone/dimethicone copolymer in aqueous emulsion, sold by Dow Corning under the reference HMW 2220 Non-Ionic Emulsion | 7.9 g, i.e. 4.76% as AM |
| Clay (Magnesium Aluminium Silicate), sold by Vanderbilt under the name Veegum granules | 1.8 g |
| Black 2 in aqueous dispersion, from Daito Kasei Kogyo under the name WD-CB2 | 9 g, i.e. 2.25% as AM |
| Water | q.s. 100 g |

0.6 g of composition A is applied, with the applicator according to the invention, to a moustache.

After a few seconds, the fibres are dry and coloured and the black colour is homogenous and persistent towards several shampooing operations.

A dyed moustache is obtained, the hairs of which are individualized and the colour of which is persistent towards washing.

The invention claimed is:

1. A method for non-permanent dyeing of human keratinous fibers, comprising applying a dyeing composition to the keratinous fibers using a container comprising a removable applicator comprising a permeable material through which the composition can pass, the composition being applied by bringing the applicator into contact with the keratinous fibers,
wherein the dyeing composition comprises:
at least one aqueous dispersion of particles of at least one hybrid hydrophobic film-forming acrylic polymer synthesized from at least one monomer having at least one (meth)acrylic acid group and/or esters of these acid monomers and/or amides of these acid monomers and from a least one styrene compound,
at least one linear block silicone copolymer present in an amount ranging from about 0.1% to about 15% by weight, relative to the total weight of the dyeing composition, and
at least one pigment.

2. The method according to claim 1, wherein the keratinous fibers are chosen from hair, roots, sidelocks, non-head hair, beard hair, moustache hair, eyelashes, and eyebrows.

3. The method according to claim 1, wherein the at least one linear block silicone copolymer is in the form of particles in dispersion in an aqueous medium.

4. The method according to claim 3, wherein the aqueous dispersion comprising the at least one linear block silicone copolymer is an aqueous dispersion of divinyldimethicone/dimethicone copolymer.

5. The method according to claim 1, wherein the at least one linear block silicone copolymer is obtained by a chain extension reaction in the presence of at least one catalyst, from at least:
(a) a polysiloxane (i) having at least one reactive group per molecule; and
(b) an organosilicone compound (ii) which reacts with the polysiloxane (i) by a chain extension reaction.

6. The method according to claim 5, wherein the polysiloxane (i) is chosen from compounds of formula (I):

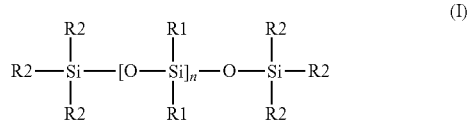

(I)

wherein $R_1$ and $R_2$ are independently chosen from hydrocarbon groups comprising from 1 to 20 carbon atoms, aryl groups and reactive groups, and n is an integer greater than 1, provided that there are on average between one and two reactive groups per polymer.

7. The method according to claim 6, wherein the reactive groups are chosen from hydrogen; aliphatically unsaturated groups; hydroxyl; alkoxy groups; alkoxyalkoxy groups; acetoxy; amino groups; and mixtures thereof.

8. The method according to claim 6, wherein $R_1$ is a methyl group and $R_2$ at the chain end is a vinyl group.

9. The method according to claim 5, wherein the organosilicone compound (ii) is chosen from polysiloxanes of formula (I) and chain-extending agents.

10. The method according to claim 9, wherein the chain-extending agents are chosen from silanes, siloxanes and silazanes.

11. The method according to claim 5, wherein the organosilicone compound (ii) is chosen from liquid organohydropolysiloxanes of formula (II):

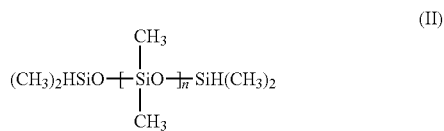

(II)

where n is an integer greater than 1.

12. The method according to claim 11, wherein n is an integer greater than 10.

13. The method according to claim 1, wherein the at least one hybrid hydrophobic film-forming acrylic polymer is chosen from styrene/acrylate copolymers resulting from the polymerization of at least one styrene monomer and of at least one $C_1$-$C_{10}$ alkyl acrylate monomer.

14. The method according to claim 1, wherein the at least one aqueous dispersion of particles of at least one hybrid hydrophobic film-forming acrylic polymer is present in the dyeing composition in an amount, as polymeric active materials, ranging from about 0.1% to about 30% by weight, relative to the total weight of the dyeing composition.

15. The method according to claim 1, wherein the at least one hybrid hydrophobic film-forming acrylic polymer and the at least one linear block silicone copolymer are present in the dyeing composition in a ratio by weight, as active materials, ranging from about 0.2 to about 10.

16. The method according to claim 1, wherein the at least one pigment is present in the dyeing composition in an amount ranging from about 0.01% to about 30% by weight, relative to the total weight of the dyeing composition.

17. The method according to claim 1, wherein the dyeing composition further comprises at least one inorganic thickening agent chosen from clays.

18. The method according to claim 1, wherein the application of the dyeing composition is optionally followed by drying the keratin fibers.

19. A device containing a non-permanent dyeing composition comprising:
at least one aqueous dispersion of particles of at least one hybrid hydrophobic film-forming acrylic polymer synthesized from at least one monomer having at least one (meth)acrylic acid group and/or esters of these acid monomers and/or amides of these acid monomers and from a least one styrene compound,
at least one linear block silicone copolymer present in an amount ranging from about 0.1% to about 15% by weight, relative to the total weight of the dyeing composition, and
at least one pigment,
wherein the device comprises a container comprising a removable applicator comprising a permeable material through which the dyeing composition can pass; and a removable stopper fitted to the removable applicator on the container.

* * * * *